(12) United States Patent
Slivka et al.

(10) Patent No.: US 7,901,435 B2
(45) Date of Patent: Mar. 8, 2011

(54) ANCHORING SYSTEMS AND METHODS FOR CORRECTING SPINAL DEFORMITIES

(75) Inventors: Michael A. Slivka, Taunton, MA (US); Hassan A. Serhan, S. Easton, MA (US); Peter Newton, San Diego, CA (US)

(73) Assignee: Depuy Spine, Inc., Raynham, MA (US)

( * ) Notice: Subject to any disclaimer, the term of this patent is extended or adjusted under 35 U.S.C. 154(b) by 4 days.

(21) Appl. No.: 10/709,795

(22) Filed: May 28, 2004

(65) Prior Publication Data

US 2005/0277919 A1 Dec. 15, 2005

(51) Int. Cl.
*A61B 17/70* (2006.01)
(52) U.S. Cl. .......................... 606/264; 606/266
(58) Field of Classification Search ............. 606/61, 606/72, 73
See application file for complete search history.

(56) References Cited

U.S. PATENT DOCUMENTS

| | | | |
|---|---|---|---|
| 4,854,304 A | 8/1989 | Zielke | |
| 4,946,458 A | 8/1990 | Harms et al. | |
| 5,002,542 A | 3/1991 | Frigg | |
| 5,207,678 A | 5/1993 | Harms | |
| 5,217,461 A | 6/1993 | Asher | |
| 5,344,422 A | 9/1994 | Frigg | |
| 5,360,431 A | 11/1994 | Puno et al. | |
| 5,403,314 A | 4/1995 | Currier | |
| 5,429,639 A | 7/1995 | Judet | |
| 5,474,555 A * | 12/1995 | Puno et al. ............ | 606/61 |
| 5,486,174 A | 1/1996 | Fournet Fayard | |
| 5,545,166 A * | 8/1996 | Howland ............... | 606/61 |
| 5,562,660 A | 10/1996 | Grob | |
| 5,672,176 A | 9/1997 | Biedermann | |
| 5,690,630 A * | 11/1997 | Errico et al. ........... | 606/61 |
| 5,725,528 A * | 3/1998 | Errico et al. ........... | 606/61 |
| 5,728,098 A | 3/1998 | Sherman | |
| 5,782,831 A | 7/1998 | Sherman | |
| 5,879,350 A | 3/1999 | Sherman | |
| 5,951,553 A | 9/1999 | Betz | |
| 5,954,725 A | 9/1999 | Sherman | |
| 6,022,350 A | 2/2000 | Ganem et al. | |
| 6,050,997 A * | 4/2000 | Mullane ............... | 606/61 |
| 6,053,917 A | 4/2000 | Sherman | |
| 6,063,090 A * | 5/2000 | Schlapfer ............. | 606/270 |
| 6,083,226 A | 7/2000 | Fiz | |

(Continued)

FOREIGN PATENT DOCUMENTS

DE 4107480 A1 * 9/1992

(Continued)

OTHER PUBLICATIONS

Betz, Randal R., et al. "An Innovative Technique of Vertebral Body Stapling for the Treatment of Patients With Adolescent Idiopathic Scoliosis: A Feasibility, Safety, and Utility Study" SPINE, vol. 28, No. 20S, pp. S255-S265 (2003).

(Continued)

*Primary Examiner* — Thomas C Barrett
*Assistant Examiner* — Michael J Araj (57) ABSTRACT

Spinal anchoring methods and devices are provided that are effective to correct spinal deformities while allowing some flexibility to the spine. In particular, the methods and devices allow a spinal fixation element to mate to several adjacent vertebrae to maintain the vertebrae at a fixed distance relative to one another, yet to allow the orientation of each vertebrae relative to the fixation element to adjust as the orientation of the patient's spine changes.

32 Claims, 5 Drawing Sheets

U.S. PATENT DOCUMENTS

| Patent | Date | Name | Ref |
|---|---|---|---|
| 6,099,528 A | 8/2000 | Saurat | |
| 6,102,912 A | 8/2000 | Cazin | |
| 6,248,106 B1 | 6/2001 | Ferree | |
| 6,287,308 B1 | 9/2001 | Betz | |
| 6,296,643 B1 | 10/2001 | Hopf | |
| 6,299,613 B1 | 10/2001 | Ogilvie | |
| 6,309,391 B1 * | 10/2001 | Crandall et al. | 606/61 |
| 6,325,805 B1 | 12/2001 | Ogilvie | |
| 6,436,099 B1 | 8/2002 | Drewry | |
| 6,471,705 B1 | 10/2002 | Biedermann | |
| 6,478,798 B1 | 11/2002 | Howland | |
| 6,485,491 B1 | 11/2002 | Farris | |
| 6,520,963 B1 | 2/2003 | McKinley | |
| 6,551,320 B2 | 4/2003 | Lieberman | |
| 6,565,569 B1 * | 5/2003 | Assaker et al. | 606/61 |
| 6,616,669 B2 | 9/2003 | Ogilvie | |
| 6,623,484 B2 | 9/2003 | Betz | |
| 6,641,586 B2 | 11/2003 | Varieur | |
| 6,695,843 B2 | 2/2004 | Biedermann | |
| 6,723,100 B2 | 4/2004 | Biedermann | |
| 6,755,829 B1 | 6/2004 | Bono | |
| 6,783,527 B2 | 8/2004 | Drewry | |
| 6,843,791 B2 | 1/2005 | Serhan | |
| 6,905,500 B2 | 6/2005 | Jeon | |
| 6,986,771 B2 | 1/2006 | Paul | |
| 6,989,011 B2 | 1/2006 | Paul | |
| 7,018,378 B2 | 3/2006 | Biedermann | |
| 7,066,937 B2 | 6/2006 | Shluzas | |
| 7,081,116 B1 | 7/2006 | Carly | |
| 7,081,117 B2 | 7/2006 | Bono | |
| 7,083,621 B2 | 8/2006 | Shaolian | |
| 7,087,057 B2 | 8/2006 | Konieczynski et al. | |
| 7,090,674 B2 | 8/2006 | Doubler | |
| 7,125,426 B2 | 10/2006 | Moumene | |
| 7,144,396 B2 | 12/2006 | Shluzas | |
| 7,204,838 B2 | 4/2007 | Jackson | |
| 7,211,086 B2 | 5/2007 | Biedermann | |
| 7,223,268 B2 | 5/2007 | Biedermann | |
| 7,264,621 B2 | 9/2007 | Coates | |
| 7,276,069 B2 | 10/2007 | Biedermann | |
| 7,291,151 B2 | 11/2007 | Alvarez | |
| 7,291,153 B2 | 11/2007 | Glascott | |
| 7,335,202 B2 | 2/2008 | Matthis | |
| 7,367,978 B2 | 5/2008 | Drewry | |
| 7,604,653 B2 | 10/2009 | Kitchen | |
| 7,621,912 B2 | 11/2009 | Harms | |
| 7,621,940 B2 | 11/2009 | Harms | |
| 7,651,515 B2 | 1/2010 | Mack | |
| 7,717,941 B2 | 5/2010 | Petit | |
| 7,727,258 B2 | 6/2010 | Graf | |
| 7,727,259 B2 | 6/2010 | Park | |
| 7,731,749 B2 | 6/2010 | Biedermann | |
| 2002/0019636 A1 | 2/2002 | Ogilvie | |
| 2002/0032443 A1 * | 3/2002 | Sherman et al. | 606/61 |
| 2002/0151900 A1 * | 10/2002 | Glascott | 606/73 |
| 2002/0173791 A1 * | 11/2002 | Howland | 606/61 |
| 2003/0004512 A1 * | 1/2003 | Farris et al. | 606/61 |
| 2003/0023243 A1 * | 1/2003 | Biedermann et al. | 606/73 |
| 2003/0045879 A1 * | 3/2003 | Minfelde et al. | 606/61 |
| 2003/0083657 A1 | 5/2003 | Drewry | |
| 2003/0100896 A1 | 5/2003 | Biedermann | |
| 2003/0153911 A1 * | 8/2003 | Shluzas | 606/61 |
| 2003/0163133 A1 * | 8/2003 | Altarac et al. | 606/61 |
| 2003/0220643 A1 | 11/2003 | Ferree | |
| 2004/0049190 A1 * | 3/2004 | Biedermann et al. | 606/61 |
| 2004/0068258 A1 | 4/2004 | Schlapfer | |
| 2004/0106921 A1 | 6/2004 | Cheung | |
| 2004/0172025 A1 | 9/2004 | Drewry | |
| 2004/0186474 A1 * | 9/2004 | Matthis et al. | 606/61 |
| 2004/0260284 A1 | 12/2004 | Parker | |
| 2005/0065516 A1 | 3/2005 | Jahng | |
| 2005/0143737 A1 | 6/2005 | Pafford | |
| 2005/0165396 A1 | 7/2005 | Fortin | |
| 2005/0177157 A1 | 8/2005 | Jahng | |
| 2005/0203513 A1 | 9/2005 | Jahng | |
| 2005/0216003 A1 * | 9/2005 | Biedermann et al. | 606/61 |
| 2005/0261686 A1 | 11/2005 | Paul | |
| 2005/0277922 A1 | 12/2005 | Trieu | |
| 2005/0288672 A1 | 12/2005 | Ferree | |
| 2006/0009768 A1 | 1/2006 | Ritland | |
| 2006/0106381 A1 | 5/2006 | Ferree | |
| 2006/0149228 A1 | 7/2006 | Schlapfer | |
| 2006/0149241 A1 | 7/2006 | Richelsoph | |
| 2006/0195098 A1 | 8/2006 | Schumacher | |
| 2006/0200131 A1 | 9/2006 | Chao | |
| 2006/0235393 A1 | 10/2006 | Bono | |
| 2006/0264935 A1 | 11/2006 | White | |
| 2006/0264937 A1 | 11/2006 | White | |
| 2006/0276791 A1 | 12/2006 | Shluzas | |
| 2006/0290183 A1 | 12/2006 | Yann | |
| 2006/0293666 A1 | 12/2006 | Matthis | |
| 2007/0049933 A1 | 3/2007 | Ahn | |
| 2007/0049937 A1 | 3/2007 | Matthis | |
| 2007/0055238 A1 | 3/2007 | Biedermann | |
| 2007/0055240 A1 | 3/2007 | Matthis | |
| 2007/0055241 A1 | 3/2007 | Matthis | |
| 2007/0073291 A1 | 3/2007 | Cordaro | |
| 2007/0118117 A1 | 5/2007 | Altarac | |
| 2007/0129729 A1 | 6/2007 | Petit | |
| 2007/0161996 A1 | 7/2007 | Biedermann | |
| 2007/0208344 A1 | 9/2007 | Young | |
| 2007/0225707 A1 | 9/2007 | Wisnewski | |
| 2007/0233064 A1 | 10/2007 | Holt | |
| 2007/0233080 A1 | 10/2007 | Na | |
| 2007/0233085 A1 | 10/2007 | Biedermann | |
| 2007/0260246 A1 | 11/2007 | Biedermann | |
| 2007/0270813 A1 | 11/2007 | Garamszegi | |
| 2008/0009862 A1 | 1/2008 | Hoffman | |
| 2008/0015578 A1 | 1/2008 | Erickson | |
| 2008/0021469 A1 | 1/2008 | Holt | |
| 2008/0058812 A1 | 3/2008 | Zehnder | |

FOREIGN PATENT DOCUMENTS

| | | |
|---|---|---|
| EP | 0879579 | 11/1998 |
| WO | WO-93/22989 A1 | 11/1993 |
| WO | 960157291 | 5/1996 |
| WO | WO-01/03570 A2 | 1/2001 |

OTHER PUBLICATIONS

Dwyer, A. F. "Experience of Anterior Correction of Scoliosis" Anterior Correction of Scoliosis, No. 93, pp. 191-206 (Jun. 1973).

Dwyer, A. F., et al. "Anterior Approach to Scoliosis" The Journal of Bone and Joint Surgery, vol. 56B, No. 2, pp. 218-224 (May 1974.

Piggott Harry, "Growth Modification in the Treatment of Scoliosis", Orthopedics, vol. 10/No. 6, pp. 945-952 (Jun. 1987).

Poulin, F, "Biomechanical Modeling of Instrumentation for the Sciolotic Spine Using Flexible Elements: A Feasability Study", Ann Chir., 1998, vol. 52(8), pp. 761-7 (abstract only).

Betz, Randal, "Comparison of Anterior and Posterior Instrumentation for Correction of Adolescent Thoracic Idiopathic Scoliosis", Spine, Feb. 1, 1999, vol. 24(3), pp. 225-39, Lippincott Williams & Wilkins.

* cited by examiner

ANCHORING SYSTEMS AND METHODS FOR CORRECTING SPINAL DEFORMITIES

FIELD OF THE INVENTION

The present invention relates to non-fusion methods and devices for correcting spinal deformities.

BACKGROUND OF THE INVENTION

Spinal deformities, which include rotation, angulation, and/or curvature of the spine, can result from various disorders, including, for example, scoliosis (abnormal curvature in the coronal plane of the spine), kyphosis (backward curvature of the spine), and spondylolisthesis (forward displacement of a lumbar vertebra). Early techniques for correcting such deformities utilized external devices that apply force to the spine in an attempt to reposition the vertebrae. These devices, however, resulted in severe restriction and in some cases immobility of the patient. Thus, to avoid this need, several rod-based techniques were developed to span across multiple vertebrae and force the vertebrae into a desired orientation.

In rod-based techniques, one or more rods are attached to the vertebrae at several fixation sites to progressively correct the spinal deformity. The rods are typically precurved to a desired adjusted spinal curvature. Wires can also be used to pull individual vertebra toward the rod. Once the spine has been substantially corrected, the procedure typically requires fusion of the instrumented spinal segments.

While several different rod-based systems have been developed, they tend to be cumbersome, requiring complicated surgical procedures with long operating times to achieve correction. Further, intraoperative adjustment of rod-based systems can be difficult and may result in loss of mechanical properties due to multiple bending operations. Lastly, the rigidity and permanence of rigid rod-based systems does not allow growth of the spine and generally requires fusion of many spine levels, drastically reducing the flexibility of the spine.

Accordingly, there remains a need for improved methods and devices for correcting spinal deformities.

BRIEF SUMMARY OF THE INVENTION

The present invention provides various embodiments of spinal anchoring methods and devices for correcting spinal deformities. In one exemplary embodiment, a spinal anchoring device is provided having a bone-engaging member that is adapted to engage bone, and a receiver member that is movably coupled to the bone-engaging member and that is adapted to seat a spinal fixation element. The anchoring device can also include a fastening element, such as a set screw, that is adapted to mate to the receiver member to lock a fixation element in a fixed position relative to the receiver member while allowing the receiver member to move freely relative to the bone-engaging member.

The receiver member can have a variety of configurations, but in one exemplary embodiment the receiver member includes a recess formed in a proximal portion thereof that is adapted to seat a spinal fixation element. The recess is preferably spaced apart and separate from the cavity in the distal portion of the receiver member. The receiver member can also include a distal portion that is movably mated to the bone-engaging member, and a proximal portion having a recess formed therein for seating a spinal fixation element. Movement of the receiver member relative to the bone-engaging member can vary, and in one embodiment the bone-engaging member can be pivotally coupled to the receiver member such that the receiver member pivots along an axis relative to the bone-engaging member. By way of non-limiting example, a pin member can extend through a distal end of the receiver member and through a proximal end of the bone-engaging member for pivotally mating the receiver member and the bone-engaging member. In another embodiment, the bone-engaging member can be polyaxially coupled to the receiver member. By way of non-limiting example, the bone-engaging member can include a spherical head formed on a proximal end thereof, and the receiver member can include a cavity formed in a distal portion thereof that is adapted to polyaxially seat the spherical head of the bone-engaging member. In other aspects, portions of the receiver member and/or the bone-engaging member can optionally include a surface coating, such as titanium oxide, nitride, or a cobalt-chrome alloy, that is adapted to facilitate movement of the receiver member relative to the bone-engaging member.

In another embodiment of the present invention, a spinal anchoring system is provided having a spinal fixation element, a spinal anchoring device having a bone-engaging member and a receiver member freely movably coupled to the bone-engaging member and configured to receive the spinal fixation element, and a fastening element that is receivable within the receiver member of the spinal anchoring device and that is configured to lock the spinal fixation element to the spinal anchoring device. The spinal fixation element can have a variety of configurations, and suitable spinal fixation elements include, for example, cables, tethers, rigid spinal rods, or flexible spinal rods. The spinal fixation can also be formed from a variety of materials include, for example, stainless steel, titanium, non-absorbable polymers, absorbable polymers, and combinations thereof.

In other embodiments the present invention provides a method for correcting spinal deformities that includes the step of implanting a plurality of anchoring devices into adjacent vertebrae in a spinal column. Each anchoring device preferably includes a bone-engaging member that is fixedly attached to the vertebra and a receiver member that is freely movable relative to the bone-engaging member and the vertebra. A spinal fixation element is then coupled to the receiver member on each anchoring device such that the fixation element extends between each of the adjacent vertebrae. Once properly positioned, the spinal fixation element is locked to the receiver member on each anchoring device to maintain the adjacent vertebrae at a fixed distance relative to one another while allowing free movement of each vertebrae in the fixed position.

BRIEF DESCRIPTION OF THE DRAWINGS

The invention will be more fully understood from the following detailed description taken in conjunction with the accompanying drawings, in which.

DETAILED DESCRIPTION OF THE INVENTION

The present invention generally provides spinal anchoring methods and devices that are effective to correct spinal deformities while allowing some flexibility to the spine. In particular, the methods and devices allow a spinal fixation element to mate to several adjacent vertebrae to maintain the vertebrae at a fixed distance relative to one another, yet to allow the orientation of each vertebrae in that fixed position to adjust as the orientation of the patient's spine changes, e.g., due to movement and/or growth. While various techniques can be used to provide for such a configuration, an exemplary anchoring device in accordance with one embodiment of the present invention generally includes a bone-engaging member that is adapted to be implanted in a vertebra, and a receiver member that is movably coupled to the bone-engaging member and that is effective to mate to a spinal fixation element. In use, when several anchoring devices are implanted within adjacent vertebrae in a patient's spine and a spinal fixation element is fixedly mated to each anchoring device, the spinal fixation element is effective to maintain the adjacent vertebrae at a desired fixed distance relative to one another. Each vertebra can, however, change orientations in that fixed position relative to the spinal fixation element because the bone-engaging member implanted therein is movably attached to the receiver member mated thereto and mated to the spinal fixation element. As a result, the spinal anchoring devices allow movement of the patient's spine. Such a technique can be advantageous for shortening and/or halting growth of the patient's spine, however the methods and devices can be used in a variety of other spinal applications. By way of non-limiting example, the device can be used for posterior dynamization to function as a decompressive device for stenosis and/or an adjunct to an intervertebral disc to unload the facets of the vertebra.

FIGS. 1A-1D illustrate one exemplary embodiment of a spinal anchoring device 10 that includes a receiver member 12 that is polyaxially coupled to a bone-engaging member 14. While the bone-engaging member 14 can have a variety of configurations, in this embodiment the bone-engaging member 14 is in the form of a polyaxial screw having a threaded shank 14b and a substantially spherical head 14a. The proximal end of the head 14a, in the illustrated embodiment, may be truncated to form a flattened proximal surface 14c that facilitates polyaxial movement of the bone engaging member 14 relative to the receiver member 12, as will be discussed in more detail below. The head 14a can also include a driver-receiving element formed in the flattened proximal end 14c for mating with a driver device. The driver-receiving element can be, for example, a socket 14d (FIGS. 1C-1D) formed within the proximal end 14c of the head 14a for receiving a driver tool which can be used to thread the bone-engaging member 14 into bone. A person skilled in the art will appreciate that virtually any device that is effective to mate to bone can be used in place of bone-engaging member 14, including, for example, screws, hooks, bolts, plates, etc., as long as the bone-engaging member 14 is movably coupled to the receiver member 12.

The receiver member 12 can also have a variety of configurations, however, in the illustrated embodiment the receiver member 12 is generally U-shaped and includes a proximal portion 12a having opposed side walls or legs 13a, 13b that are substantially parallel to one another and that define a recess 16 therebetween for seating a spinal fixation element 18. The spinal fixation element 18 can have a variety of configurations, and, by way of non-limiting example, it can be rigid, semi-rigid, bendable, flexible, etc. Suitable spinal fixation elements for use with the present invention include, by way of non-limiting example, rods, tethers, cables, plates, etc. The spinal fixation element 18 can also be formed from a variety of materials including, for example, stainless steel, titanium, non-absorbable polymers, absorbable polymers, and combinations thereof. In certain applications, it may be desirable to provide a fixation element that is flexible to allow for bending, yet that is rigid in tension such that the fixation element can not stretch or lengthen. This is particularly useful in applications where it is necessary to prevent growth of the spine while allowing normal flexibility.

Figure 1A:
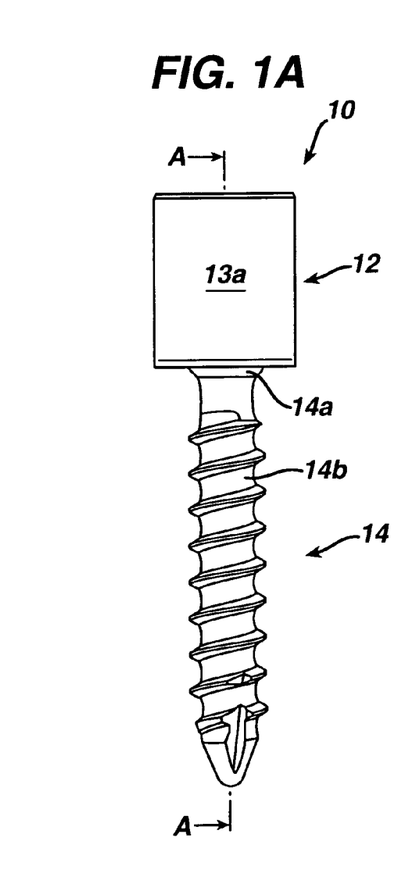
FIG. 1A is a side view of one embodiment of a spinal anchoring device in accordance with the present invention.
Figure 1B:
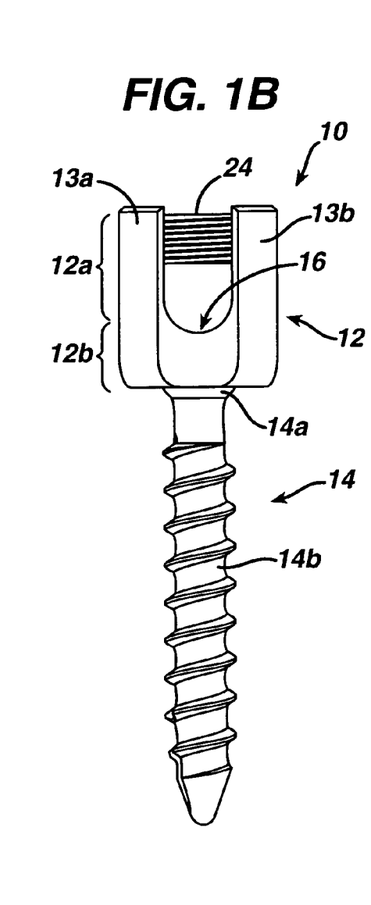
FIG. 1B is another side view of the spinal anchoring device shown in FIG. 1A.
Figure 1C:
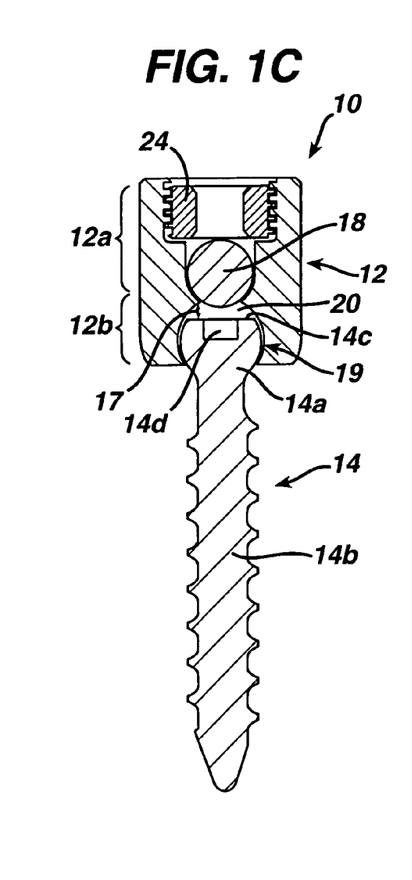
FIG. 1C is a cross-sectional view of the spinal anchoring device shown in FIG. 1A taken across line A-A.

Still referring to FIGS. 1A-1D, the receiver member 12 also includes a distal portion 12b that is adapted to movably couple to the bone-engaging member 14. In particular, the distal portion 12b may include a seat 19 that is preferably effective to receive the head 14a of the bone-engaging member 14 such that the bone-engaging member 14 is polyaxially movable relative to the receiver member 12. In the illustrated embodiment, the seat 19 is defined by at least a portion of the walls of a substantially spherical cavity 20 formed in the distal portion 12b. The seat 19 is preferably complementary in shape to the head 14a. For example, in the illustrated embodiment, the seat 19 and the head 14a are spherical in shape. One skilled in the art will appreciate, however, that the seat 19 and head 14a need not be spherical in shape or complementary in shape; the seat 19 and head 14a may have any shape(s) sufficient to allow polyaxial motion of the bone engaging member 14 relative to the receiver member 12. As discussed above, in certain embodiments the proximal end of the head 14a may be truncated to facilitate polyaxial motion. As shown in FIG. 1C, for example, the gap 17 between the fixation element 18 and the flattened proximal surface 14c provides an increased range of polyaxial motion to the head 14a within the cavity 20.

Figure 1D:
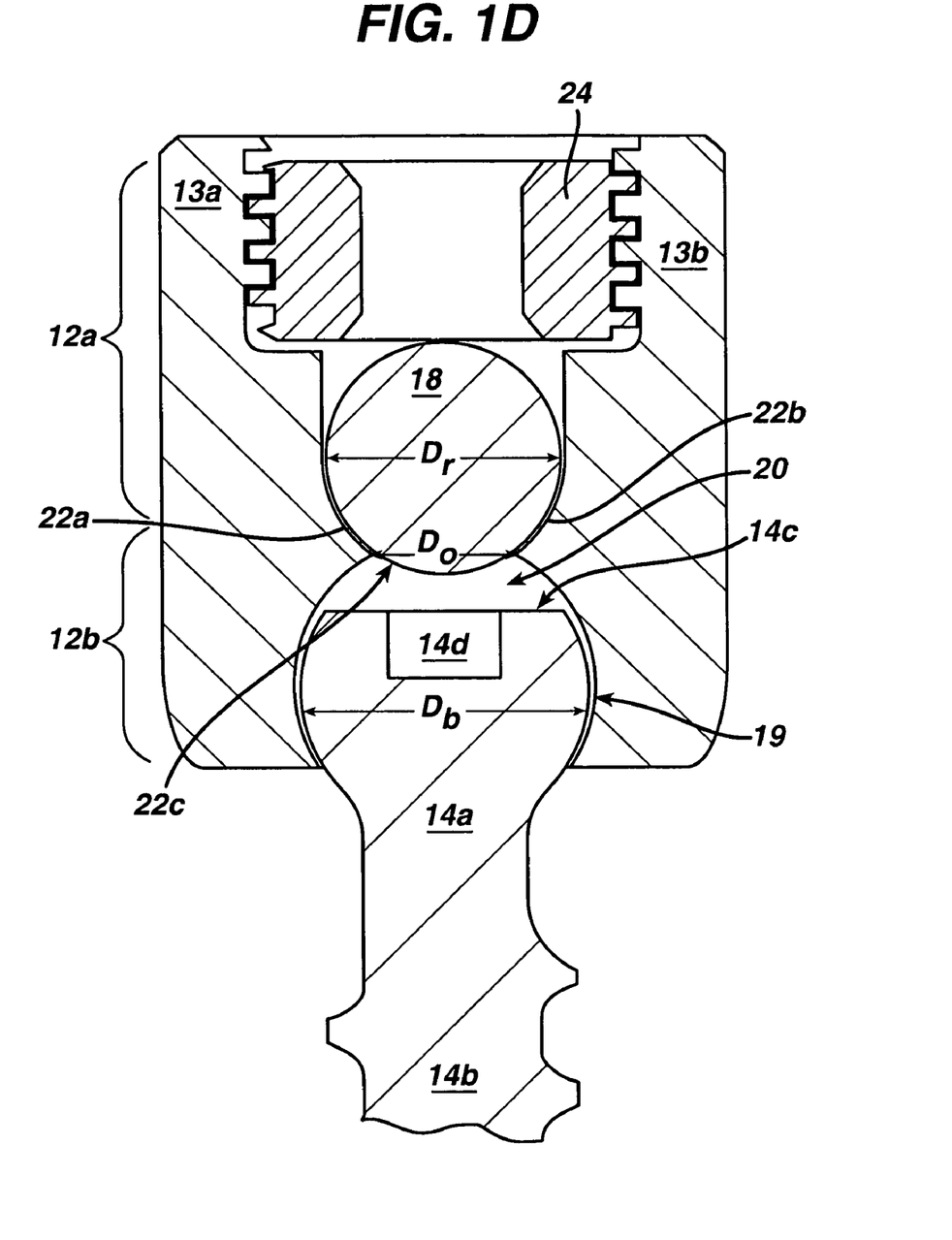
FIG. 1D is an enlarged view of a proximal portion of the spinal anchoring device shown in FIG. 1C.

In the illustrated embodiment, the cavity 20, and thus the seat 19, is spaced apart from the recess 16 in the proximal portion 12a of the receiver member 12 to inhibit contact between the head 14a and the spinal fixation element 18, thus allowing polyaxial movement of the spherical head 14a of the bone-engaging member 14 without interference from the spinal fixation element 18 disposed in the recess 16. The spacing between the recess 16 in the proximal portion 12a and the cavity 20 in the distal portion 12b can be achieved using a variety of techniques, but in the illustrated embodiment the legs 13a, 13b each include a protrusion or ridge 22a, 22b formed therein that separates the recess 16 and the cavity 20, as shown in FIGS. 1C-1D. The ridges 22a, 22b together define an opening 22c having a diameter $D_o$ that is less than both the diameter $D_r$ of the spinal fixation element 18 and the diameter $D_h$ of the spherical head 14a of the bone-engaging member 14 to prevent passage of the fixation element 18 and the head 14a therethrough, thus separating the two components.

Since the diameter $D_o$ of the opening 22c is preferably smaller than the diameter $D_h$ of the head 14a of the bone-engaging member 14, the device 10 can be adapted to allow the bone-engaging member 14 to be inserted through the proximal portion 12a of the receiver member 12 to seat the head 14a in the spherical cavity 20. This can be achieved, for example, by expanding or pulling apart the legs 13a, 13b to increase the diameter $D_o$ of the opening 22c, thereby allowing the spherical head 14a to pass therethrough. The head 14a can then seated within the cavity 22 and the legs 13a, 13b can return to their original state. The spinal fixation element 18 can then be seated in the recess 16 in the proximal portion 12a of the receiver member 12 and the ridges 22a, 22b will prevent the fixation element 18 from passing therethrough into the cavity 22. The legs 13a, 13b can thereafter be locked in a fixed position relative to one another using a locking mechanism that mates to the legs. Exemplary locking mechanisms will be described in more detail below.

Figure 1E:
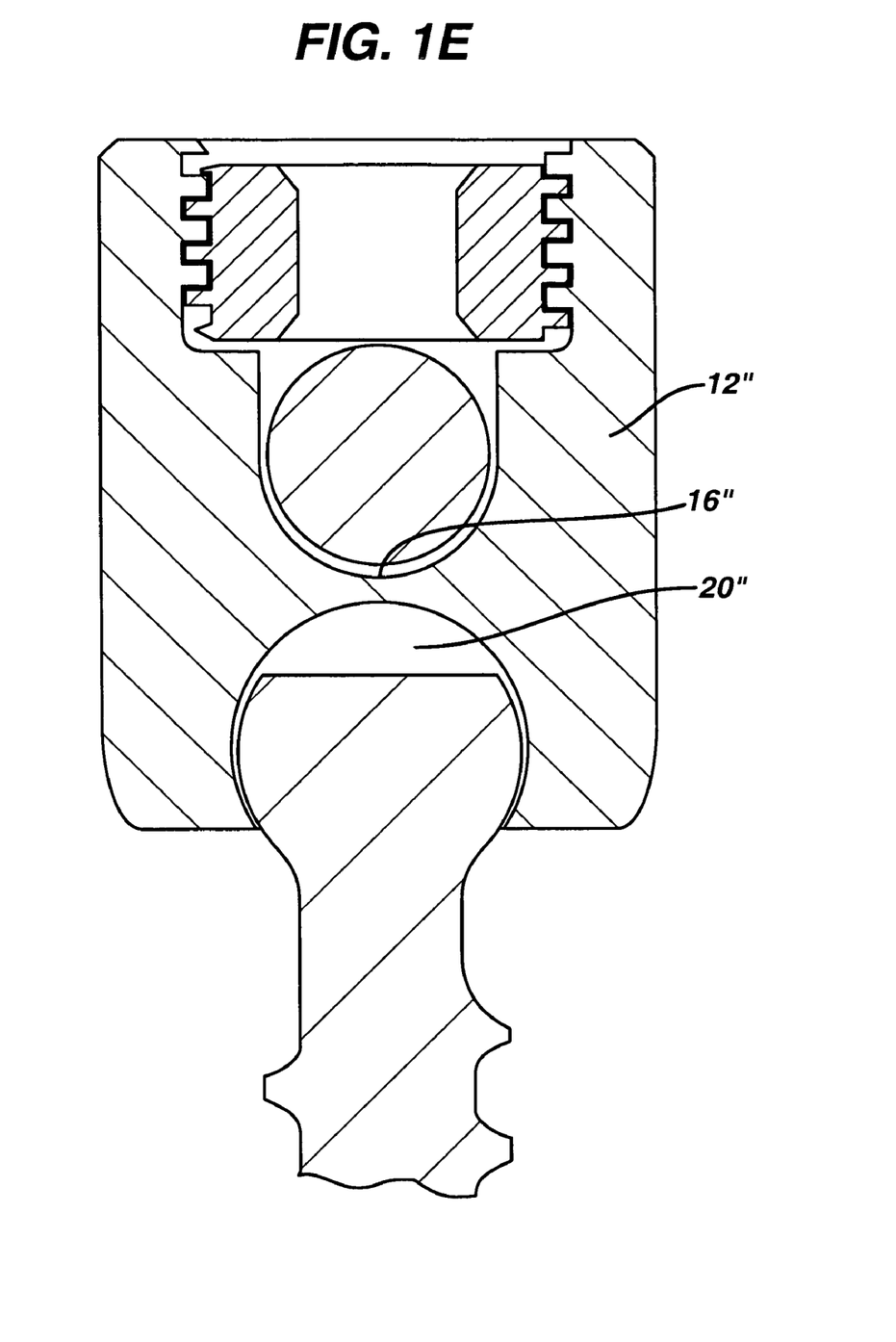
FIG. 1E is an enlarged view of a proximal portion of another embodiment of a spinal anchoring device.

In other embodiments (not shown), rather than having ridges 22a, 22b formed on the legs 13a, 13b of the receiver member 12, the receiver member 12 can include an insert that is adapted to be disposed therein after the spherical head 14a is positioned within the cavity 22 in the distal portion 12b to separate the spherical head 14a from the fixation element 18. The insert can have any shape and size, but it is preferably adapted to complete the substantially spherical cavity 20 in the distal portion 12b of the receiver member 12, and to seat a spinal fixation element 18 extending through the receiver member 12. The insert can also be configured to merely sit within the receiver member 12, or it can be adapted to mate to the receiver member 12, e.g., using threads, a snap-fit, or some other engagement technique known in the art, such that the insert is retained at a desired location in the receiver member 12. In use, the insert will allow the bone-engaging member 14 to rotate freely within the cavity 20 in the distal portion 12b of the receiver member 12 because the insert does not bear against the spherical head 14a of the bone-engaging member 12. The insert will also allow the spinal fixation element 18 to be locked within the receiver member 12 using techniques which will be discussed in more detailed below. A person skilled in the art will appreciate that a variety of other techniques can be used to allow the bone-engaging member 14 to be assembled and disassembled from the receiver member 12. By way of non-limiting example, the proximal and distal portions 12a, 12b of the receiver member 12 can be separate components that are matable to one another, e.g., using threads or other mating techniques known in the art. Such a configuration allows the head 14a of the bone-engaging member 14 to be seated within the cavity 20 in the distal portion 12b prior to mating the proximal and distal portions 12a, 12b of the receiver member 12 to one another. Other techniques not shown or described herein can also be used as long as the bone-engaging member 14 and the receiver member 12 are at least partially freely movable relative to one another. For example, in certain embodiments, the head 14a of the bone engaging member 14 may be inserted through the distal end of the receiver member 12. In such embodiments, the opening 12c may not be necessary and thus, as shown in FIG. 1E by way of non-limiting example, the cavity 20" and the recess 16" may be completely separated within the receiver member 12".

As previously indicated, the device 10 can also include a fastening element that is effective to lock the spinal fixation element 18 to the receiver member 12, and more preferably that is effective to lock the spinal fixation element 18 within the recess 16 in the receiver member 12 such that the spinal fixation element 18 cannot move relative to the receiver 12. The fastening element can have a variety of configurations, and it can be adapted to mate to inner and/or outer portions of the legs 13a, 13b on the receiver member. FIGS. 1B-1D illustrate one embodiment of a fastening element that is in the form of a threaded set screw 24 that is adapted to mate with corresponding threads formed within the receiver member 12, i.e., on the legs 13a, 13b. A person skilled in the art will appreciate that a variety of fastening elements known in the art can be used with the various spinal anchoring devices of the present invention and that the illustrated set screw 24 is merely one exemplary embodiment of a fastening element.

Figure 2:
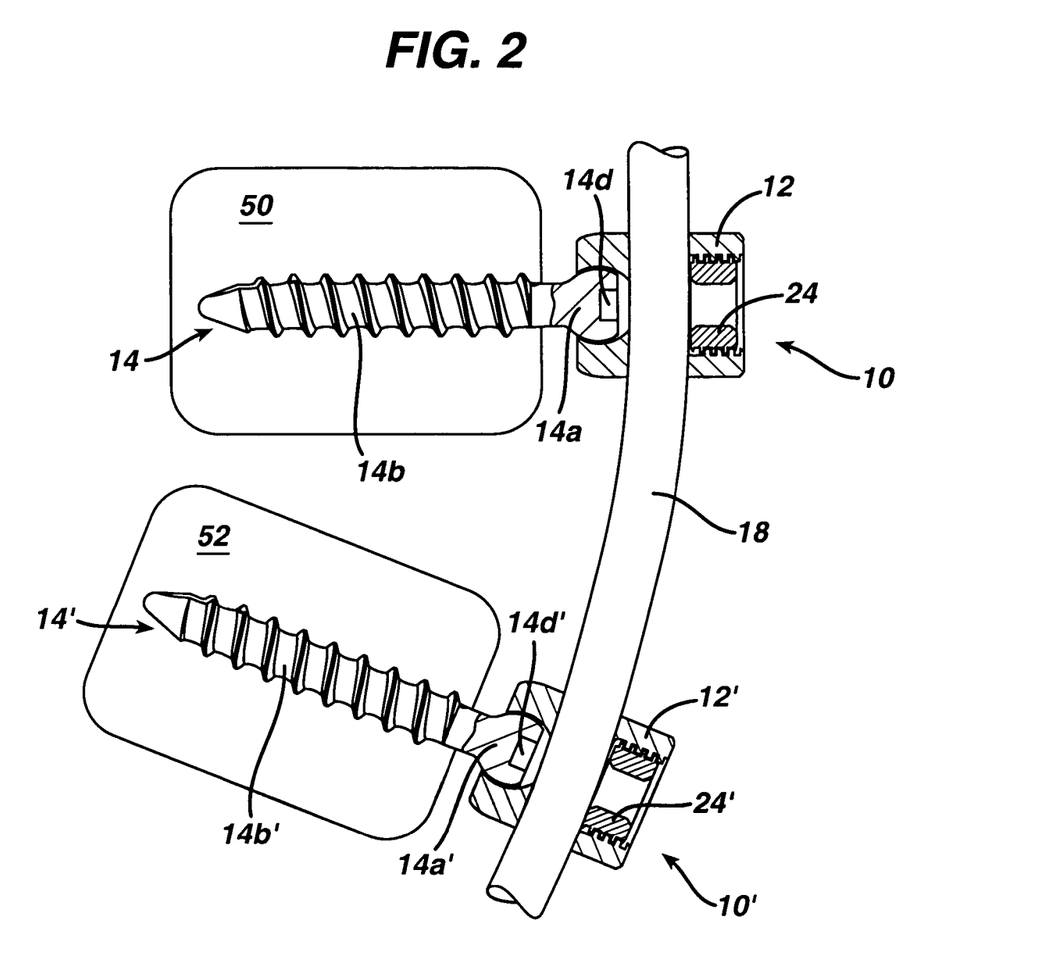
FIG. 2 is a side, partially cross-sectional view illustration of two spinal anchoring devices, as shown in FIG. 1A, implanted in adjacent vertebrae in accordance with one embodiment of a method for correcting spinal deformities.

FIG. 2 illustrates the spinal anchoring device 10 shown in FIGS. 1A-1D in use. In the illustrated embodiment, two spinal anchoring devices 10, 10' are implanted in adjacent vertebraes 50, 52, however any number of spinal anchoring devices can be used and the number will vary depending on the nature of the procedure being performed. The devices 10, 10' are implanted in the vertebrae 50, 52 by inserting the bone-engaging member 14, 14' of each device 10, 10' through the receiver member 12, 12' and then threading the bone-engaging member 14, 14' into the vertebra. As previously mentioned, this can be achieved using a driver tool that is adapted to engage a driver-receiving element, such as socket 14d, 14d', in the spherical head 14a, 14a' on each bone-engaging member 14, 14'. Once the bone-engaging members 14, 14" are implanted in the adjacent vertebrae 50, 52, a spinal fixation element, such as spinal rod 18, is positioned within the receiver member 12, 12' of each device 10, 10'. Since the devices 10, 10' are preferably used to correct a spinal deformity, the position of each vertebra will likely need to be adjusted to correct the deformity in order to seat the rod 18 within each receiver member 12, 12'. Once properly positioned, the rod 18 can be locked to each receiver member 12, 12' preferably by inserting a locking mechanism, such as a set screw, into the head of each receiver member 12, 12', thereby maintaining the vertebrae 50, 52 at a fixed distance apart from one another. Since each bone-engaging member 14, 14' is polyaxially movable relative to each receiver member 12, 12', each vertebrae 50, 52 is free to move in that fixed position relative to the receiver member 12, 12' coupled thereto, thus allowing for movement of the spine.

Figure 3A:
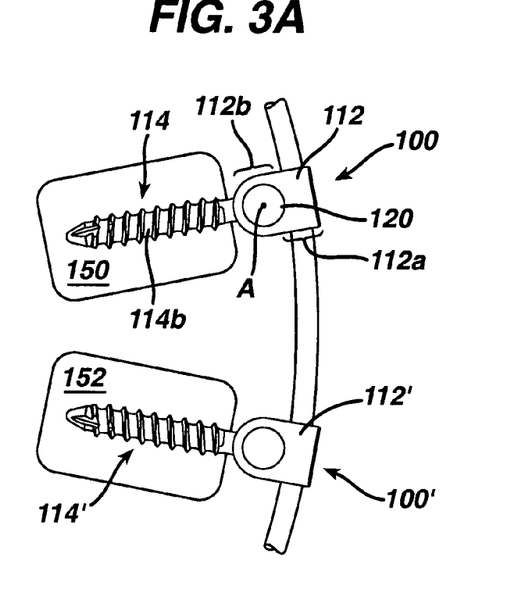
FIG. 3A is a side view illustration of two spinal anchoring devices having receiver members coupled to a spinal fixation rod and having bone-engaging members implanted in adjacent vertebrae with another embodiment of a method for correcting spinal deformities.
Figure 3B:
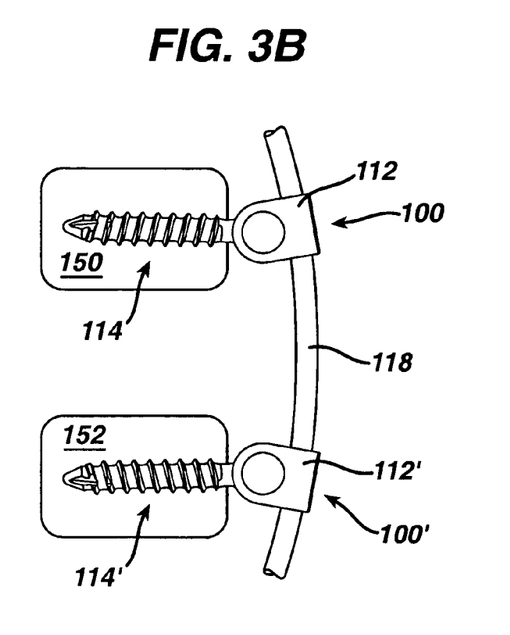
FIG. 3B illustrates the spinal anchoring devices shown in FIG. 3A with the receiver members pivoted relative to the bone-engaging members to allow for movement of the vertebrae.

FIGS. 3A-3B illustrate yet another embodiment of a spinal anchoring device 100. While the drawings illustrate two devices 100, 100' implanted in adjacent vertebrae 150, 152, the devices 100, 100' are substantially similar and those only one device 100 will be described. As shown, the device 100 is similar to device 10 in that it includes a receiver member 112 having a proximal portion 112a for seating a spinal fixation element 118, and a distal portion adapted to couple to a bone-engaging member 114. In this embodiment, however, rather than allowing polyaxial movement of the receiver member 112 relative to the bone-engaging member 114, the receiver member 112 pivots along an axis, indicated by point A, relative to the bone-engaging member 114. Pivotal movement can be achieved using a variety of techniques, and in one exemplary embodiment a bearing element can be formed between the components 112, 114. The bearing element can be, for example, a pin member 120 that extends through the distal portion 112b of the receiver member 112 and through a portion of the bone-engaging member 114. Since the bone-engaging member 114 is not polyaxial, the bone-engaging member 114 may or may not include a head formed thereon, and thus the pin member 120 can extend through a head of the bone-engaging member 114, or it can extend directly through a portion of the shaft 114b of the bone-engaging member 114. A person skilled in the art will appreciate that a variety of other techniques can be used to provide a receiver member 112 that is pivotally coupled to a bone-engaging member 114.

In use, several devices 100 can be implanted in adjacent vertebrae to maintain the vertebrae in a fixed position relative to one another, yet to allow pivotal movement of each vertebrae in that fixed position, e.g., to allow the patient's spine to flex. As shown in FIGS. 4A-4B, two devices 100, 100' are implanted in adjacent vertebra 150, 152. In FIG. 4A, the vertebrae 150, 152 are maintained in a first, fixed position by locking spinal rod 118 to the receiver member 112, 112' of each device 100, 100'. In FIG. 4B, the vertebrae 150, 152 have pivoted within that fixed position due to flexion of the patient's spine, and thus each bone-engaging member 114, 114' has pivoted along axis A relative to the receiver member 112, 112' coupled thereto, and relative to the spinal fixation element 18 mated to each receiver member 112, 112'. Such a configuration can be useful in applications where movement along a single plane, such as the patient's coronal plane, is desired while preventing axial rotation of the vertebrae 150, 152.

The spinal anchoring devices in accordance with various embodiments of the present invention can be formed from a variety of materials, including, for example, stainless steel, titanium, cobalt-chrome alloys, etc. In other embodiments, the spinal anchoring devices can include features to facilitate movement of the bone-engaging member relative to the receiver member. For example, referring to the device 10 shown in FIGS. 1A-1D, portions of the bone-engaging member 14 and the receiver member 12 that come into contact with one another, e.g., the spherical head 14a of the bone-engaging member 14 and/or the cavity 20 in the receiver member 12, can include a surface coating thereon or therein. The surface coating can be formed from a material that allows free movement of the components 12, 14, and that is preferably wear-resistant. By way of non-limiting example, suitable materials include titanium oxide, nitride, and a cobalt-chrome alloy.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A spinal anchoring device, comprising:
a bone-engaging member adapted to engage bone, the bone-engaging member having a head formed thereon;
a spinal fixation element;
a U-shaped receiver member having a distal cavity that movably seats the head of the bone-engaging member and the U-shaped receiver member having a proximal recess that seats the spinal fixation element, the cavity and the recess including an opening extending therebetween and defined by the U-shaped receiver member, the opening further having a size that allows a portion of the spinal fixation element to extend into the distal cavity but prevents passage therethrough of the spinal fixation element seated in the proximal recess; and
a fastening element adapted to mate to the U-shaped receiver member to lock the spinal fixation element relative to the U-shaped receiver member while allowing the U-shaped receiver member to move freely relative to the bone-engaging member.

2. The spinal anchoring device of claim 1, wherein the bone-engaging member is pivotally coupled to the head of the U-shaped receiver member such that the U-shaped receiver member pivots along an axis relative to the bone-engaging member.

3. The spinal anchoring device of claim 2, further comprising a pin member extending through a distal end of the U-shaped receiver member and through a proximal end the head of the bone-engaging member for pivotally mating the U-shaped receiver member and the bone-engaging member.

4. The spinal anchoring device of claim 2, further comprising a surface coating on portions of the bone-engaging member and the U-shaped receiver member that come into contact with one another.

5. The spinal anchoring device of claim 4, wherein the surface coating is formed from a material selected from the group consisting of titanium oxide, nitride, and a cobalt-chrome alloy.

6. The spinal anchoring device of claim 1, wherein the bone-engaging member is polyaxially coupled to the U-shaped receiver member.

7. The spinal anchoring device of claim 6, wherein the head on the bone-engaging member comprises a spherical head that is formed on a proximal end thereof, and wherein the cavity is adapted to polyaxially seat the spherical head of the bone-engaging member.

8. The spinal anchoring device of claim 1, wherein the fastening element is adapted to mate to a proximal portion of the U-shaped receiver member to engage and lock a spinal fixation element within the recess in the U-shaped receiver member.

9. The spinal anchoring device of claim 8, wherein the fastening element comprises a set screw adapted to mate with corresponding threads formed within at least a portion of the recess in the U-shaped receiver member.

10. A spinal anchoring system, comprising:
a spinal fixation element;
a spinal anchoring device having a bone-engaging member with a head formed thereon and a U-shaped receiver member having a cavity that freely movably seats the head of the bone-engaging member in a distal portion of the cavity and that is configured to receive the spinal fixation element in a proximal portion of the cavity, the proximal and distal portions of the cavity being spaced apart by opposed protrusions defined by the U-shaped receiver member that allow a portion of a spinal fixation element to extend into the distal portion of the cavity but prevent contact between the bone-engaging member and the spinal fixation element; and
a fastening element receivable within the U-shaped receiver member of the spinal anchoring device and being configured, when mated to the U-shaped receiver member, to lock the spinal fixation element to the spinal anchoring device while allowing free movement of the U-shaped receiver member relative to the bone-engaging member.

11. The spinal anchoring system of claim 10, wherein the U-shaped receiver member is pivotally coupled to the head of the bone-engaging member.

12. The spinal anchoring system of claim 11, further comprising a bearing element formed between the U-shaped receiver member and the bone-engaging member for allowing pivotal movement of the U-shaped receiver member relative to the bone-engaging member.

13. The spinal anchoring system of claim 12, wherein the bearing element includes a surface coating adapted to facilitate movement of the U-shaped receiver member relative thereto.

14. The spinal anchoring system of claim 13, wherein the surface coating is formed from a material selected from the group consisting of titanium oxide, nitride, and a cobalt-chrome alloy.

15. The spinal anchoring system of claim 10, wherein the bone-engaging member is polyaxially coupled to the U-shaped receiver member.

16. The spinal anchoring system of claim 15, wherein the head on the bone-engaging member comprises a spherical head formed thereon, and wherein the cavity is configured to receive the spherical head.

17. The spinal anchoring system of claim 10, wherein the head of the bone-engaging member is coupled to a distal end of the U-shaped receiver member, and the fastening element is matable to a proximal end of the U-shaped receiver member.

18. The spinal anchoring system of claim 17, wherein the fastening element includes threads formed thereon for mating with corresponding threads formed within at least a portion of the recess formed in the U-shaped receiver member.

19. The spinal anchoring system of claim 10, wherein the spinal fixation element is selected from the group consisting of a cable, a tether, a rigid spinal rod, and a flexible spinal rod.

20. The spinal anchoring system of claim 10, wherein the spinal fixation element is formed from a material selected from the group consisting of stainless steel, titanium, non-absorbable polymers, absorbable polymers, and combinations thereof.

21. A method for correcting spinal deformities, comprising:
    implanting a plurality of anchoring devices into adjacent vertebrae in a spinal column, each anchoring device including a bone-engaging member that is fixedly attached to the vertebra and a U-shaped receiver member having a distal cavity that seats a head formed on the bone-engaging member such that the U-shaped receiver member is freely movable relative to the bone-engaging member and the vertebra;
    coupling a spinal fixation element to a proximal recess in the U-shaped receiver member on each anchoring device such that the fixation element extends between each of the adjacent vertebrae, the cavity and the recess of the U-shaped receiver member including an opening extending therebetween and defined by the U-shaped receiver member, the opening further having a size that allows a portion of a spinal fixation element to extend into the cavity but prevents passage of the spinal fixation element therethrough;
    locking the spinal fixation element to the U-shaped receiver member on each anchoring device to maintain the adjacent vertebrae at a fixed distance relative to one another, the spinal fixation element being seated in the opening but prevented from contacting the bone-engaging member, thereby allowing free movement of each U-shaped receiver member relative to each bone-engaging member.

22. The method of claim 21, wherein the U-shaped receiver member of at least one of the anchoring devices is movable along a single plane relative to the bone-engaging member.

23. The method of claim 21, wherein the bone-engaging member of at least one of the anchoring devices is polyaxially coupled to the U-shaped receiver member.

24. The method of claim 21, wherein the head on the bone-engaging member comprises a spherical head formed on a proximal end thereof, and wherein the cavity is adapted to polyaxially seat the spherical head of the bone-engaging member.

25. The method of claim 21, wherein the U-shaped receiver member includes a distal portion movably mated to the head of the bone-engaging member, and a proximal portion having the recess formed therein for seating the spinal fixation element.

26. The method of claim 21, wherein the step of locking comprises applying a fastening element to each U-shaped receiver member to engage and lock the spinal fixation element therein.

27. The method of claim 21, wherein the spinal fixation element is selected from the group consisting of a cable, a tether, a rigid spinal rod, and a flexible spinal rod.

28. A spinal anchoring device, comprising:
    a bone screw having a head and a shank;
    a spinal fixation element;
    a U-shaped receiver member having a distal seat for receiving at least a portion of the head of the bone screw, a proximal seat formed on an internal surface thereof that receives the spinal fixation rod, and opposed protrusions that define an opening between the distal seat and the proximal seat that allows a portion of the spinal fixation element to extend into the distal seat but that prevents passage therethrough of the spinal fixation element seated in the proximal seat; and
    a fastening element adapted to mate to the U-shaped receiver member to seat the spinal fixation rod in the proximal seat, the proximal seat being spaced a distance apart from the distal seat sufficient to allow polyaxial motion of the bone screw relative to the U-shaped receiver member upon seating of the spinal fixation rod in the proximal seat by the fastening element.

29. The spinal anchoring device of claim 28, wherein the U-shaped receiver member includes a recess extending from a proximal opening in the U-shaped receiver member, a distal portion of the recess defining the proximal seat for the spinal fixation rod.

30. The spinal anchoring device of claim 29, wherein the fastening element is a set screw having external threads for engaging internal threads provided in the recess.

31. A spinal anchoring device, comprising:
    a bone-engaging member adapted to engage bone, the bone-engaging member having a head formed thereon;
    a U-shaped receiver member having a distal cavity that movably seats the head of the bone-engaging member and having a proximal recess that is adapted to seat a spinal fixation element, the distal cavity and the proximal recess including an opening extending therebetween and having a size that prevents passage therethrough of a spinal fixation element seated in the proximal recess; and
    a fastening element adapted to mate to the U-shaped receiver member to lock a fixation element relative to the U-shaped receiver member while allowing the U-shaped receiver member to move freely relative to the bone-engaging member.

32. The spinal anchoring device of claim 31, wherein the opening is defined by the U-shaped receiver member.

* * * * *

UNITED STATES PATENT AND TRADEMARK OFFICE
CERTIFICATE OF CORRECTION

| | | |
|---|---|---|
| PATENT NO. | : 7,901,435 B2 | Page 1 of 1 |
| APPLICATION NO. | : 10/709795 | |
| DATED | : March 8, 2011 | |
| INVENTOR(S) | : Slivka et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 80 days.

Signed and Sealed this
Twenty-eighth Day of June, 2011

David J. Kappos
*Director of the United States Patent and Trademark Office*